United States Patent [19]
Williams

[11] Patent Number: 6,045,517
[45] Date of Patent: Apr. 4, 2000

[54] DIAGNOSTIC APPARATUS AND METHOD FOR EVALUATION OF CARPAL TUNNEL SYNDROME

[76] Inventor: George Roger Williams, 3024 SE. 40th St., Edmond, Okla. 73013

[21] Appl. No.: 09/056,512

[22] Filed: Apr. 7, 1998

Related U.S. Application Data

[63] Continuation-in-part of application No. 08/709,857, Sep. 10, 1996, abandoned.

[51] Int. Cl.[7] .................................................. A61B 5/103
[52] U.S. Cl. ........................................ 600/587; 600/595
[58] Field of Search .................................. 600/587, 588, 600/595; 482/47, 44, 45, 48; 601/40; 602/21, 22; 73/379.01, 379.02; 269/329, 265, 266; 128/878; 5/647

[56] References Cited

U.S. PATENT DOCUMENTS

| | | | |
|---|---|---|---|
| 4,641,832 | 2/1987 | Mattox | 482/47 |
| 4,774,966 | 10/1988 | Lemmen | 600/587 |
| 4,986,280 | 1/1991 | Marcus et al. | |
| 5,136,743 | 8/1992 | Pirela-Cruz | 5/647 |
| 5,163,443 | 11/1992 | Fry-Welch | |
| 5,263,490 | 11/1993 | Hayes et al. | 600/588 |
| 5,275,174 | 1/1994 | Cook | 600/587 |
| 5,471,996 | 12/1995 | Boatright et al. | 600/587 |
| 5,800,561 | 9/1998 | Rodriguez | 623/26 |

*Primary Examiner*—Richard J. Apley
*Assistant Examiner*—Justine R. Yu
*Attorney, Agent, or Firm*—James F. Harvey, III

[57] ABSTRACT

This invention is a diagnostic device for measuring the extensibility of certain key carpal ligaments so as to determine the tendency of the subject to carpal tunnel damage. It consists of a structure to secure the arm and hand in a predetermined position on a stationary platform and the metacarpals of the hand in a predetermined position on a carriage moveable relative to the platform, so that the radius and ulnar bones of the forearm may be aligned in a fixed plane parallel with the moveable plane of the metacarpals of the hand. Once secure, a force is applied to the carriage in a dorsal direction perpendicular to the metacarpal plane, so as to measure the metacarpal glide. This force places stress on the ligaments of the volar joint between the proximal and distal carpal row, and resulting displacement, tension, and creep strength values are measured by a load cell and a lineometer. Using these values, the following can be determined: (1) extent of volar carpal ligament contracture and deformity; (2) requirements of ligament retraining; (3) diagnostic criteria for predicting carpal tunnel syndrome; and (4) values to assist health professionals in determining whether or not surgery for decompressing peripheral neuropathy is warranted.

12 Claims, 4 Drawing Sheets

DIAGNOSTIC APPARATUS AND METHOD FOR EVALUATION OF CARPAL TUNNEL SYNDROME

CROSS-REFERENCES TO RELATED APPLICATIONS

This application is a continuation-in-part of inventor's U.S. patent application, Ser. No. 08/709,857, filed on Sep. 10, 1996, now abandoned. This application is incorporated herein by this reference.

STATEMENT AS TO RIGHTS TO INVENTIONS MADE UNDER FEDERALLY SPONSORED RESEARCH AND DEVELOPMENT

This invention was made in the performance of a Cooperative Research and Development Agreement with the Department of the Air Force, identified by USAF CRDA Number 95-OC-01, Oklahoma City Air Logistics Center (OC-ALC), Tinker Air Force Base, Oklahoma. The invention may be manufactured and used by or for the Government of the United States for all governmental purposes without any payment of any royalty.

BACKGROUND

A. Field of the Invention

This invention relates generally to medical diagnostic devices. More particularly, the present invention provides an apparatus and a method for measuring the tension of carpal ligaments under applied translation forces which in turn will provide indicators of future or existing carpal tunnel syndrome.

B. Theory of the Invention

Carpal tunnel syndrome is a condition in which the median nerve is compressed by the surrounding contents of the median nerve canal. This condition is believed to be caused by a biomechanical ligament imbalance in the volar carpal ligaments, which is in turn related to the increased ratio of power produced by the flexor muscles over extensor muscles as they interact with the hand.

The flexor muscle tendons of the forearm acting on the wrist, fingers and thumb exert a collective static force power many times greater, volarly, than the extensor muscle tendons acting to stabilize the same members of the wrist and hand dorsally. The ratio of these opposing forces is normally four to one. However, work demands often increase this ratio through hypertrophy of the flexor muscle tendon units by intensity and duration of tasks requiring dominantly finger, thumb, and wrist function.

The effect of the volar flexor forces, acting upon the palmer transverse carpal ligament (PCTL) as a pulley, attenuate the PCTL and apply forces anteriorly and medially. This places traction forces to the ligament ends of the carpus. Each night, while the muscles are at rest, the intercarpal segments restore their normal position grossly; however, some minute anteriomedial deformity occurs, and slack of the PCTL is concurrently taken up by contractile forces of the ligament(s). Numerous cycles of force followed by rest develop an established deforming characteristic narrowing the horeshoe ends of the carpal tunnel, which are held in position by a thickening PTCL and other volar carpal ligaments. Simultaneously, the PTCL acting as a pulley concentrates the load of the finger and thumb function initiating a volar glide, that is, movement as a unit in a volar direction, of the carpal metacarpal complex. This volar glide of the carpal metacarpal complex attenuates the predisposed thin dorsal carpal ligaments (DCL) originating from the distal radial ulna (DRU). The volar carpal ligaments collectively, non stressed, begin to contract, encouraging the anteriomedial collapse of the intercarpal spaces.

Flexor power exerts applied forces to the moment arm of a joint whose motion occurs in the direction of the muscle origin regulated by an interplay of antagonists, pulleys and joint alignment. A variation of one or more serves to simplify convergence towards a direct line to the point of origin and shorten the distance between. Either the force is expressed in efficiency or a decreasing biomechanical advantage occurs by a volar shift of the axis of the proximal carpal row. This may account for the propensity of carpal tunnel patients to develop odd compensatory behaviors like flexing the wrist during power grasping, conceivably to account for the change in position of the more volar placed PTCL. Carpal tunnel volume is reduced and any other predispositon will hasten onset of the painful condition known as carpal tunnel syndrome.

Thus, the resistance of the PCTL and related volar ligaments to movement returning the carpal metacarpal complex to a neutral position, i.e. dorsal glide, should be indicative of the severity of the condition of carpal tunnel syndrome or the propensity of the subject to incur the condition.

C. Description of the Related Art

There are numerous systems in the prior art for measuring forces exerted by the forearm, wrist, and fingers. One such system is described in U.S. Pat. No. 5,163,443, by Fry-Welch et al. (Nov. 17, 1992). It describes a system for measuring volitional forces applied by the hand, wrist, and forearm of a living person. A method for correlating the forces exerted in a plurality of directions so that they can be measured by a single force transducer is described. The system measures muscle force exerted by the wrist and forearm motions and correlates these to the forces required to do specific work tasks which contribute to Carpal Tunnel Syndrome. However, this system does not include or teach a mechanism for immobilizing the wrist in relation to the forearm so that measurements relative to these two body components can be made. Also, the invention described by Fry-Welch measures volitional muscular forces; there is no provision for applying an outside force, measuring the resistance of passive components, such as the ligaments, and measuring positional joint alignment in an anterior posterior plane.

An article by Jobbins, Bird, and Wright, entitled "A Joint Hyperextensometer for the Quantification of Joint Laxity", Engineering in Medicine, Vol 8 No. 2, 1979, describes a device for measuring the magnitude of joint laxity of the fifth metacarpo-phalangeal (MCP) joint. The device consists of immobilizing the joint so that the angle of displacement of the joint from the zero baseline can be measured. A mechanical slipping clutch exerts a predetermined force on the joint. However, these measurements are applicable to the areas of rheumatic arthritis and osteoarthrosis, and not carpal tunnel syndrome. They are taken with relation to the MCP joint and not the carpal joint. The measurement taken is one of force versus angle of movement in a single plane; joint alignment, which involves the normal displacement between two different planes, is not discussed. They conclude by stating that, in the test population, laxity at the MCP joint of the index finger reflects joint laxity elsewhere in the body; this observation would not hold true for such conditions as carpal tunnel syndrome which are caused by repetitive and cumulative motions by a particular joint of the body.

Marcus et al., U.S. Pat. No. 4,986,280, teaches a mechanism for sensing the relative angular orientation of two relatively movable joint segments of a living body joined together at a joint, focusing primarily on the fingers and thumb. However, it does not measure the orientation of the planes of the hand and forearm with one another or specifically address the carpal joint.

The previous methods for measuring the conditions which precipitate carpal tunnel syndrome have the following disadvantages:

1. They concentrate on measuring muscular force which is voluntarily exerted in a repetitive fashion rather than the resistive forces of the ligaments and joints.
2. They do not predict the onset or the degree of damage or malalignment leading to carpal tunnel syndrome.
3. They do not measure forces exerted on the carpal joint.
4. They do not immobilize the forearm and wrist in such a way that one can measure the orientation between these two components in terms of the displacement between the planes of the wrist and forearm.

For the foregoing reasons, a new method and apparatus is needed for measuring the conditions which lead to carpal tunnel syndrome so as to predict the onset of the condition, isolate the anatomical areas which are pertinent to the condition, and which is non invasive.

SUMMARY

The present invention is directed to an apparatus to measure in a non-invasive manner the relative resistive force of carpal ligaments which in turn serves to predict the onset and intensity of carpal tunnel syndrome. In order to perform the required measurements, the apparatus is comprised of a means for stabilizing the forearm in conformance with a fixed first vertical plane; a means for separately stabilizing the carpal metacarpal complex in conformance with a moveable second vertical plane which is parallel to the first vertical plane; a means by which the second vertical plane may be moved in a direction normal to the fixed first vertical plane; and a means for applying and measuring force and/or displacement encountered in moving the second vertical plane in relation to the fixed first vertical plane.

It is therefore an object of this invention to provide a new diagnostic device for measuring the extent of carpal tunnel syndrome in afflicted patients by measuring the amount of resistance, or force, exhibited by the volar carpal ligaments of the carpal joint over time and displacement of the joint in a dorsal direction.

It is a further object of this invention to apply force to specific points on the carpal metacarpal complex by means of vertical pins placed at critical points which isolate the joint to be measured from other interactions.

It is a further object of this invention to measure the resistive force exhibited by the volar ligaments in the carpal joint at various values of dorsal glide, or normal displacement of the second vertical plane with relation to the first vertical plane, over time.

It is a further object of this invention to measure the relaxation of the volar ligaments, or creep, where such relaxation gradually becomes more pronounced for dorsally applied force.

Further objects and advantages of this invention will become more readily apparent upon reference to the following detailed description of a preferred embodiment, as illustrated in the accompanying drawings.

INDEX

10 Base Plate
11 Carriage Base
12 Saddle Base
13 Carriage Base Channel
20 Vertical Rod
21 Cushioning Sleeve
22 Vertical Sliding Rod
23 Quad Nut
24 V-Slide
25 V-Slide Slot
26 Hexagonal Nut
27 Proximal Slot
28 Distal Slot
30 Base Forearm Axis
31 Base Palmar Axis
32 Forearm Axis
33 Palmar Axis
40 Proximal Stationary Pin
41 Distal Stationary Pin
42 Proximal Slideable Pin
43 Distal Slideable Pin
44 Proximal MCP Pin
45 Distal MCP Pin
46 Proximal Left Forearm Pin
47 Distal Left Forearm Pin
48 Proximal Right Forearm Pin
49 Distal Right Forearm Pin
70 Threaded Rod
71 Threaded Bore
72 Control Support Bracket
73 Knurled Knob
74 Hexagonal Bolt
75 Threaded Orifice
76 Face Plate
77 Holding Screw
78 Cushioning Washer
79 Brass Cylinder
80 Cavity
81 Face Plate Screws
82 Load Cell
83 Load Cell Mounting Bracket
84 Load Cell Screw
85 Lock Washer 86 Spacer
87 Sensor Output Lug
88 Lineometer
89 Bracket
89 Sensing Wire
90 Electrical Wires
92 Electronic Measurement Device

DESCRIPTION OF THE PREFERRED EMBODIMENTS

Figure 1:
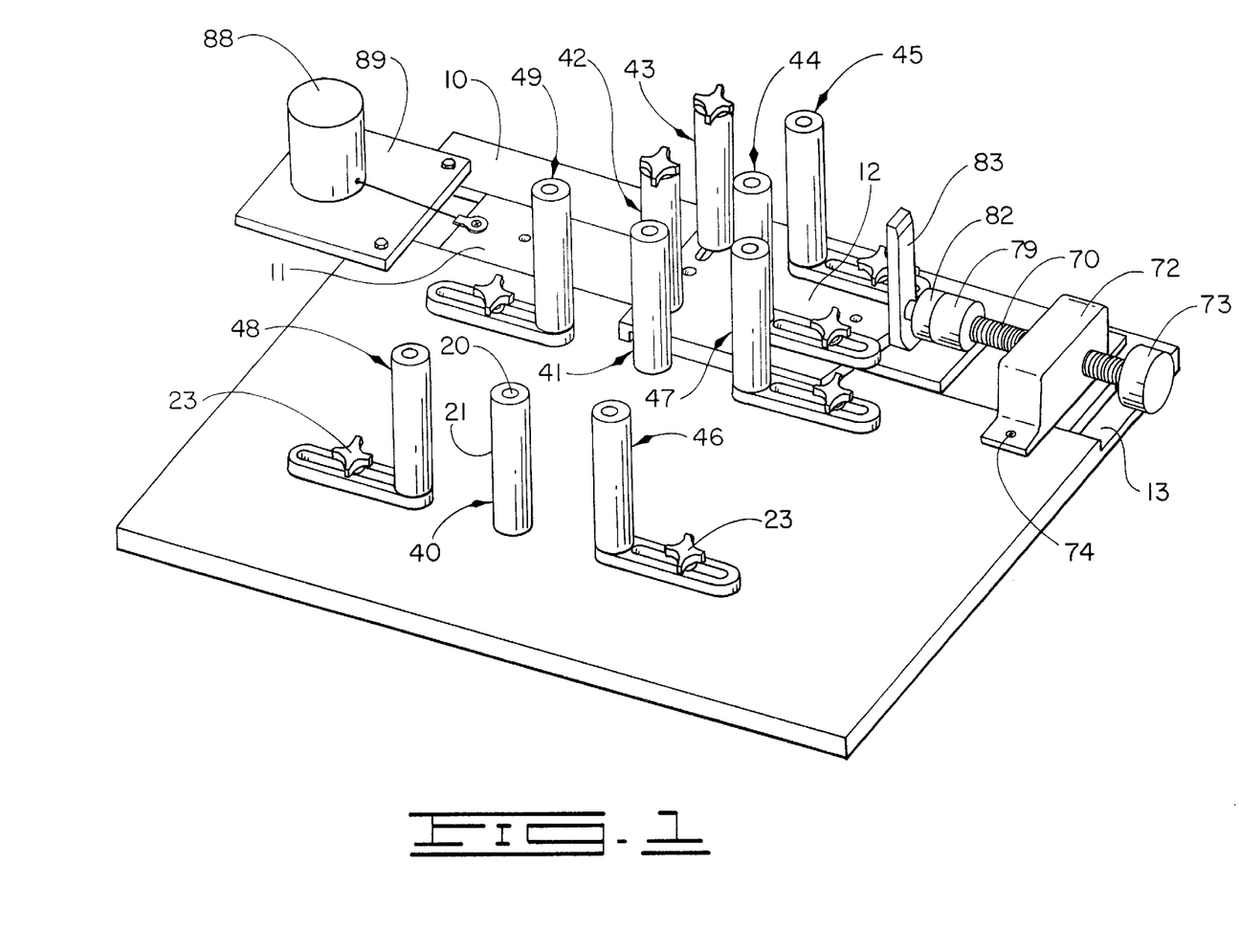
FIG. 1 shows a perspective view of an embodiment of the invention showing its major components.

FIG. 1 shows a general perspective view of the measurement apparatus. All components are supported by a horizontally oriented, rectangular base plate 10 for portability of the apparatus, for maintaining a stationary platform on which measurements may be taken, and for maintaining alignment of all components of the apparatus to a fixed frame of reference. Base plate 10 is described as being rectangular solely to aid in the description of the alignment of the parts of the apparatus and may be any reasonable shape.

Ten vertical pins are employed to align the subject's forearm, carpal, and metacarpal members to the apparatus. These pins are approximately four (4) inches long and occur in the apparatus in three configurations, i.e. stationary, slideable, and adjustable. In the subsequent description of pin placement and configuration, reference will be made to the pins as they apply to measurements of the subject's left forearm and carpal metacarpal complex.

Figure 2:
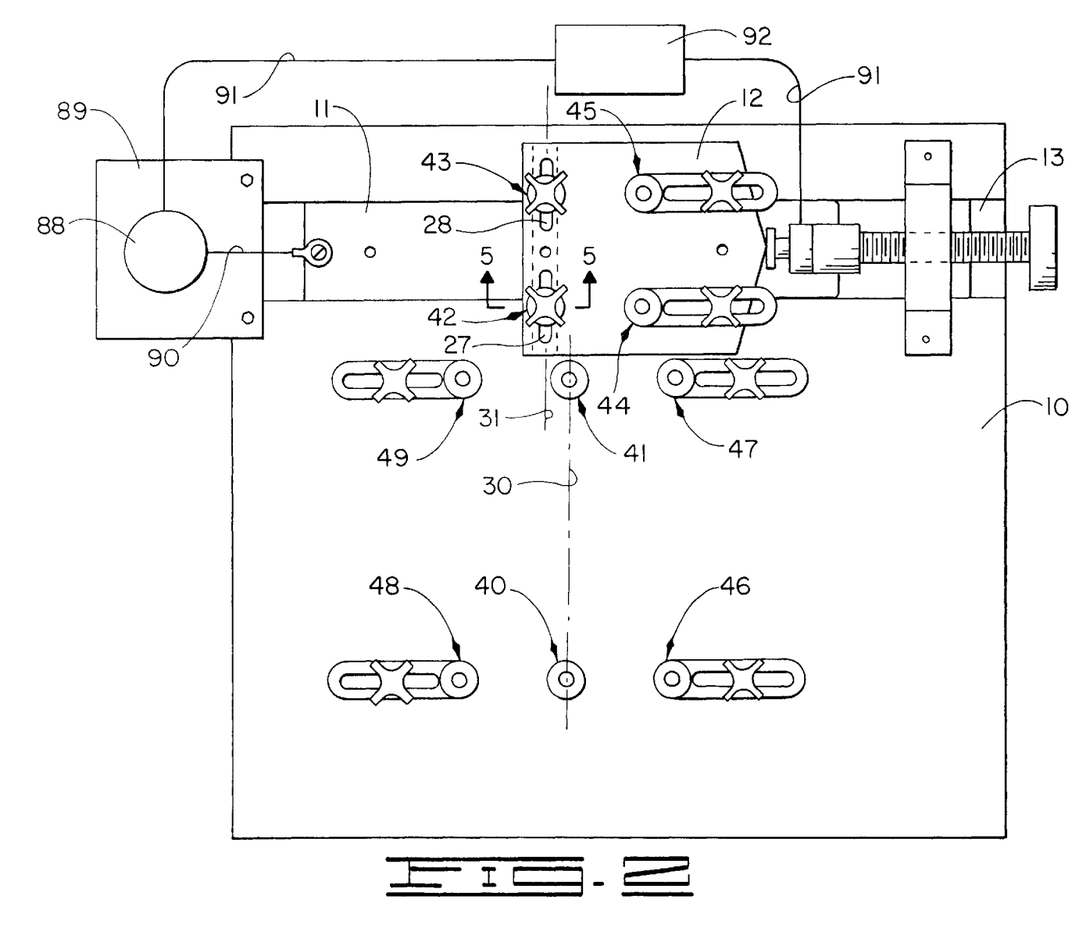
FIG. 2 shows a top view of the same embodiment of the invention.

Two stationary pins, namely, the proximal stationary pin 40 and the distal stationary pin 41, align the subject's forearm to the apparatus. Each consists of a vertical rod with a threaded lower end which is inserted into a threaded hole in the base plate 10. Each vertical rod 20 is surrounded by a cylindrical cushioning sleeve 21 which supports the forearm in a comfortable manner. The cushioning sleeve may be made of any soft material, such as foam or rubber. With reference to FIG. 2, the line between the proximal stationary pin 40 and the distal stationary pin 41 and parallel to the sides of the base plate 10 defines the base forearm axis 30 against which is aligned the forearm axis 32 (FIG. 6) for measurement purposes. These pins define the fixed vertical plane of the forearm and establish the orientation of the forearm of the subject with the other components of the apparatus. The distance between the proximal stationary pin 40 and the distal stationary pin 41 is less than the average length of the adult radius and ulna, approximately eight inches.

Figure 4:
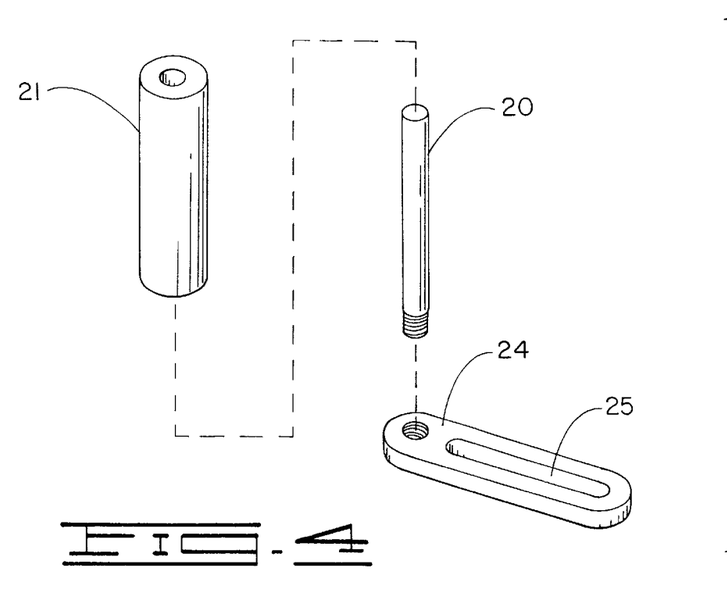
FIG. 4 shows a view of an embodiment of an adjustable pin assembly.

The apparatus includes six adjustable pins, 44, 45, 46, 47, 48, and 49 as shown in FIG. 1, each of which are constructed as shown in FIG. 4. Each of said adjustable pins includes a V-Slide 24 including a V-Slide slot 25 for securing the assembly to the base plate 10 with any suitable means, such as a quad nut 23 (as shown) and bolt, wing nut and bolt, or threaded stud. In the figure, a quad nut 23 is fixedly attached to a threaded bolt (not shown) which is inserted through the V-Slide slot 25 and received by a threaded hole in the base plate 10. The vertical rod 20 is secured to one end of the V-Slide 24 by any suitable means such as threading one end of the rod, welding, adhesive, or hexagonal nut. The V-Slide slot 25 in the V-Slide 24 is completely exposed to view when a vertical rod 20 inserted through the cushioning sleeve 21 is attached to the V-Slide 24. Two adjustable pins, the proximal left forearm pin 46 and distal left forearm pin 47, firmly and proximally secure the forearm to the apparatus and align the ulna and radius of the subject's forearm with the base forearm axis 30.

The subject's carpal and metacarpal complex is supported by a carriage base 11 and a saddle base 12. The carriage base channel 13 in the base plate 10 is rectangular in cross section, the sides of which are perpendicular to the base forearm axis 30, so as to slideably receive the rectangular carriage base 11, the upper surface of said carriage base 11 being flush with the upper surface of the base plate 10.

The saddle base 12 is permanently attached to the top of the carriage base 11. Shims (not shown) on the carriage base 11 serve to elevate the saddle base 12 while keeping it parallel to the carriage base 11, so as to prevent the bottom side of the saddle base 12 from contacting the surface of base plate 10 when the carriage base 11 slides within the carriage base channel 13. Attachment may be accomplished by standard techniques commonly known in the art, such as rivets, adhesive, bolts, screws, or welding. The saddle base 12 serves as a platform holding two slideable pins, i.e. the proximal slideable pin 42 and the distal slideable pin 43, and two adjustable pins, i.e. the proximal MCP pin 44 and the distal MCP pin 45, in alignment with each another while positioning the carpal and metacarpal complex for diagnostic measurement. Further, it also allows the four pins 42, 43, 44, and 45 to move as a group in relation to the six pins 40, 41, 46, 47, 48, and 49 attached to the base plate 10, so that the dorsal displacement, or dorsal glide, of the carpal and metacarpal complex may be measured relative to the radius and ulna.

Figures 5, 6:
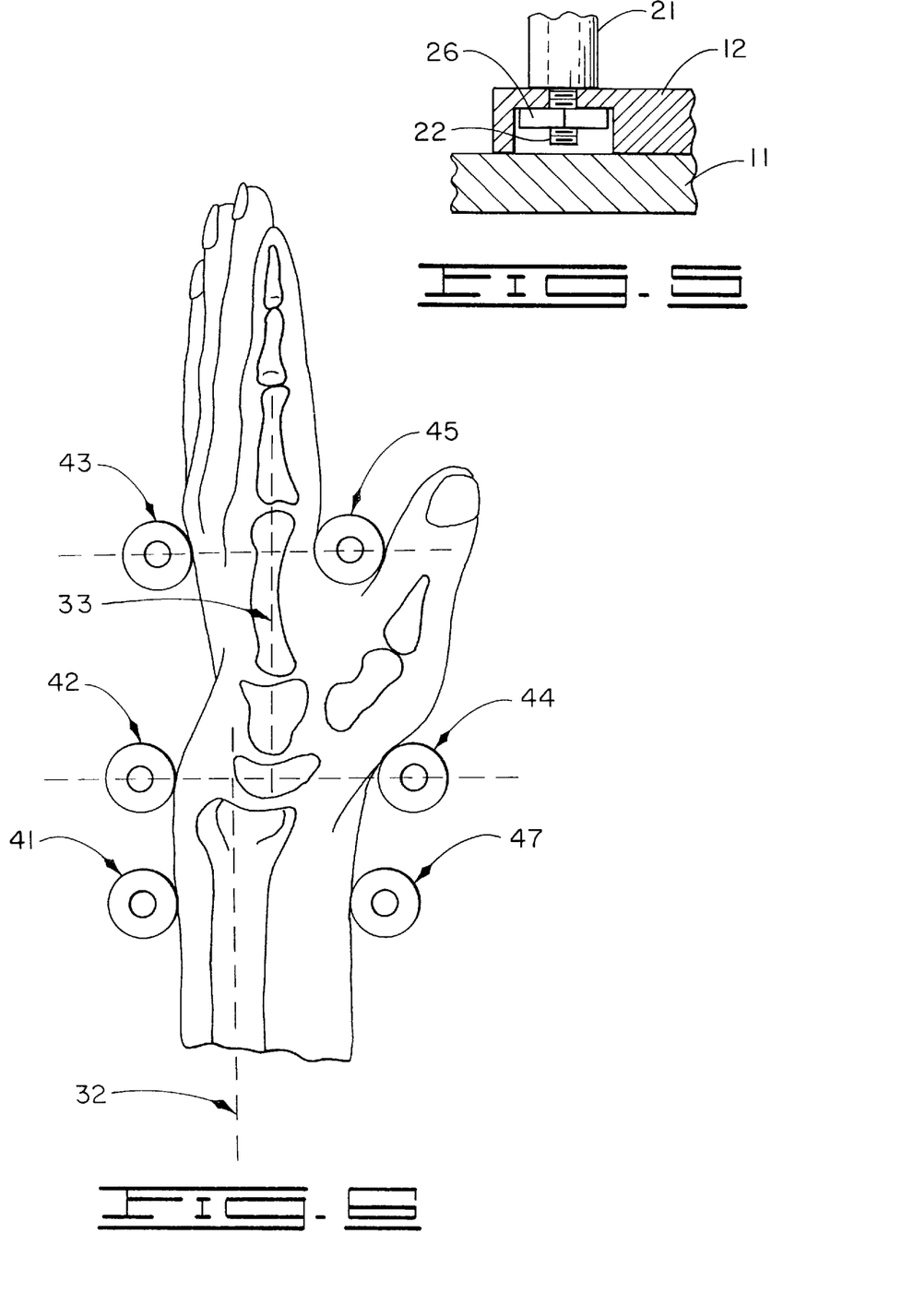
FIG. 5 shows a more detailed cross-sectional view of the attachment of a slideable pin assembly to the saddle base.
FIG. 6 shows a top view of the left hand as it is oriented to the illustrated embodiment of the invention, showing the placement of pins facilitating measurement of carpal translocation when attempting to restore normal alignment dorsally.

The saddle base 12 serves as platform for the proximal slideable pin 42 and the distal slideable pin 43, as illustrated in FIG. 2. Each of said pins includes a vertical sliding rod 22 having a central threaded stud protruding from its lower end. A quad nut 23 is permanently fixed to the upper end of the vertical sliding rod 22 so that the quad nut 23 and vertical sliding rod 22 rotate as a unit. Quad nut 23 may be attached by standard means known to the art, such as adhesive, threading, welding, or soldering. The threaded stud on the lower end of vertical sliding rod 22 is inserted through a cushioning sleeve 21 so that said sleeve fits snugly around said rod and against the base of the quad nut 23. The threaded stud of vertical sliding rod 22 of the proximal slideable pin 42 is then inserted through proximal slot 27, whose central axis is parallel with the base forearm axis 30, and captured by hexagonal nut 26, as illustrated in FIG. 5, the opposing sides of which slideably fit into a rectangular channel cut in the underside of the saddle base 12 and parallel with the base forearm axis 30. The rectangular channel constrains the hexagonal nut 26 from rotating when the quad nut 23 and vertical sliding rod 22 combination is rotated. The threaded lower end of the vertical sliding rod 22 of the distal slideable pin 43 is inserted into the distal slot 28, whose central axis is colinear with the axis of the proximal slot 27, and secured in a similar manner. The axes of the proximal slot 27 and distal slot 28 define the base palmar axis 31 and constrain movement of the proximal slideable pin 42 and the distal slideable pin 43 along said axis. The dorsal side of the left hand rests against these pin assemblies which keep the carpal and the metacarpal structures of the hand in the same plane, and these pin assemblies are slideably moveable to accommodate different sizes of hands. In order to keep the hand in a plane and to resist the natural cupping action of the hand, two adjustable pins, i.e. the proximal MCP pin 44 and the distal MCP pin 45, are firmly and proximally adjusted to the subject's carpal metacarpal complex.

A lineometer 88 is mounted on a bracket 89 astride the carriage base channel 13 with sufficient clearance to accommodate the carriage base 11 without binding, and secured to base plate 10 by two hexagonal bolts 74. The sensing wire 90 protruding from the lineometer 88 is attached to the carriage base 11 such that the wire is substantially parallel to the axis of travel of the carriage base 11. The lineometer 88 is a standard resistive device well known in the industry, in which a wire with a spring on one end is attached to the moveable arm of a potentiometer in such a way that the distance the wire is pulled out of or allowed to retract back into the lineometer is directly proportional to the resistance of the internal potentiometer. In this manner, the voltage drop across the internal potentiometer is directly proportional to the distance of movement of the protruding wire. Electrical wires 91 protruding from the lineometer casing permit the sensing of resistance, and resulting voltage drop, detected by the lineometer when the carriage base 11 is moved. These electrical wires are connected to a electronic measurement device 92. The electronic measurement device 92 presently consists of two physically separate meters, one for measuring force and one for measuring distance. However, the best mode for the electronic measurement device 92 is a single computing system accepting electronic inputs through appropriate interface units, storing the values, and performing more detailed calculations on the values. The inventor contemplates conversion to the computing system method of measurement as investigation of this concept continues.

Figure 3:
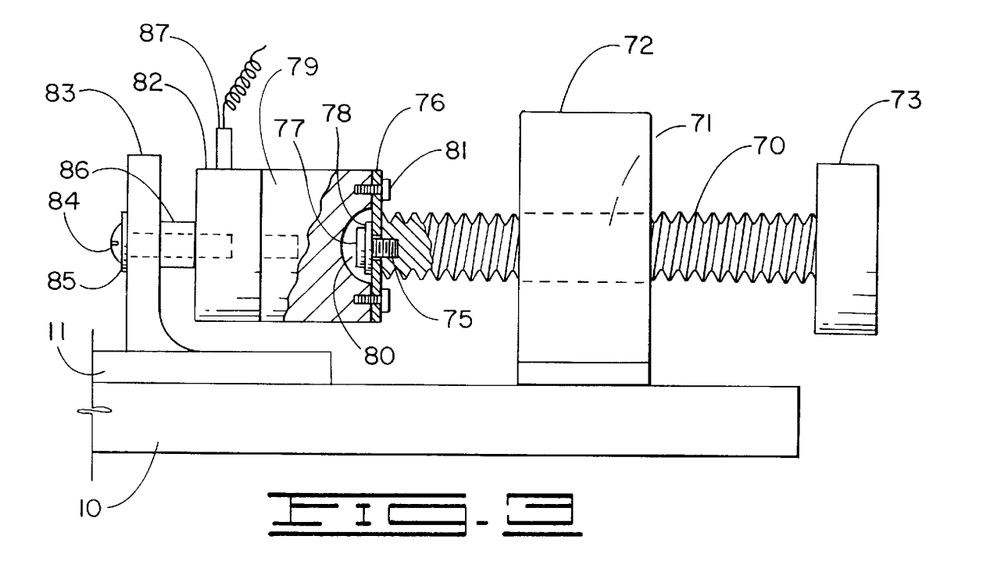
FIG. 3 shows a view of the details of an embodiment of the movement means and force measurement means.

The saddle base 12 and the carriage base 11 are made to move as a unit along the carriage base channel 13 by means of a screw assembly as illustrated in FIG. 3. A control support bracket 72 is mounted astride the carriage base channel 13 with sufficient clearance between the base of the control support bracket 72 and the upper surface of the carriage base 11 to prevent binding, and secured to the base plate 10 by two hexagonal bolts 74. The control support bracket 72 contains a threaded bore 71, the axis of which is oriented in a direction substantially parallel to the direction of movement of the carriage base 11. A threaded rod 70 having a knurled knob 73 permanently attached to its outermost end and having a threaded orifice 75 in its innermost end is helically inserted through the threaded bore 71 of the control support bracket 72 from its outermost side and brought into contact with a face plate 76. Face plate 76 has a central circular hole whose diameter is less than that of the threaded rod 70 so that said rod does not engage said central hole. A holding screw 77 is inserted through a cushioning washer 78 and the central circular hole and helically engages the threaded orifice 75 of the threaded rod 70, so that the threaded rod 70 may communicate longitudinal motion in a direction perpendicular to the base forearm axis 30 to the face plate 76 without preventing the threaded rod 70 from rotating relative to the fixed face plate 76. The face plate 76 is fixedly attached by means of three face plate screws 81, spaced equidistantly about the circumference of said face plate, to the first end of a brass cylinder 79 having the same diameter as the face plate 76 and having a concave cavity 80 in its first end which encloses the holding screw 77 without touching it. The second end of the brass cylinder 79 has a centrally placed hole which receives the threaded stud on the passive side of a load cell 82.

A load cell 82, having an active side which receives a load cell screw 84 and a passive side with a threaded stud, is fixedly supported by a load cell mounting bracket 83 attached to the carriage base 11 by two load cell mounting bracket bolts (not shown). The load cell screw 84 is inserted through a lock washer 85, a hole in the load cell mounting bracket 83, a short spacer 86, and attached to the active side of the load cell 82. The brass cylinder 79 is attached to the passive side of the load cell 82, as previously described.

The load cell 82 is a standard device well known in the industry, containing four strain gauges in a Wheatstone bridge configuration, so that the unbalance of the bridge caused by a static load is measured in terms of a voltage detected at its sensor output lug 87. Although the choice of load cell model is not critical, the best device for this application has been found to be an LCF100 tension/compression load cell obtained from Omega Technologies of Stamford, Conn. Use of such a load cell which detects both tension and compression permits force to be detected by an electronic measurement device 92 attached to the sensor output wires emanating from the sensor output lug 87 regardless of the direction of travel of the saddle base 12.

The combination of load cell 82, brass cylinder 79, and face plate 76 is held fixed to the carriage base 11 through the load cell mounting bracket 83, while the combination of threaded rod 70 and holding screw 77 is permitted to rotate as the knurled knob 73 is turned. The central axes of the load cell 82, brass cylinder 79, and threaded rod 70 are colinear and substantially parallel with the axis of travel of the carriage base 11. As the knurled knob 73 is turned, the threaded rod 70 exerts a force which is translated through the fixed load cell mounting bracket 83 to the carriage base 11 causing the carriage base 11 to move in one of two directions along the carriage base channel 13, depending upon whether the knurled knob is rotated clockwise or counter-clockwise.

To describe the operation of the apparatus, references will be made to FIG. 6 for the placement of the pins against the subject's left forearm and hand and to FIG. 1 for the relationship of the pins to the apparatus. The subject's forearm is stabilized in a neutral or hand shaking position in which the forearm axis 32 and the palmar axis 33 are parallel and coplanar. The subject's left arm is placed in a hand shaking orientation on the base plate 10 between two rows of pins, with the dorsal forearm against the row composed of the proximal stationary pin 40 and the distal stationary pin 41. The distal stationary pin 41 is positioned just proximal to the radial distal head and the ulnar styloid, and the proximal stationary pin 40 is positioned arbitrarily and proximally. The proximal left forearm pin 46 and distal left forearm pin 47 are brought into firm contact with the subject's volar forearm and tightened in place with their respective quad nuts, so that the subject's forearm is tightly secured between the four pins. The carpal metacarpal complex is captured between the four pins of the saddle base 12. The proximal slideable pin 42 located proximal the epicondyles of the metacarpals dorsally and the proximal MCP pin 44 is located exactly over the pisiform and head of the scaphoid volarly. The distal slideable pin 43 and the distal MCP pin 45 are placed proximally to the distal end of the metacarpals to stabilize the palmar axis 33 of the hand in line with the base palmar axis 31.

By positioning the pins in the aforementioned manner, the necessary means is provided to initiate force displacement of the carpus at the proximal carpal row while maintaining a parallel alignment of the metacarpals with that of the forearm throughout the procedure. This movement in the dorsal direction results in a shear maneuver between the DRU and the proximal carpal row. The displacement, or dorsal glide, and the resistive force of the carpal ligaments are measured by the electronic measurement device 92.

For measurements pertaining to the right hand, the procedure is essentially the same, except for the following. The right forearm is placed The subject's left arm is placed in a hand shaking orientation on the base plate 10 between two rows of pins, with the dorsal forearm against the row composed of the proximal stationary pin 40 and the distal stationary pin 41. The proximal right forearm pin 48 and distal right forearm pin 49 are brought into firm contact with the subject's volar forearm and tightened in place with their respective quad nuts. The carpal metacarpal complex is captured between the four pins of the saddle base 12. However, the saddle base is repositioned so that the proximal MCP pin 44 located proximal the epicondyles of the metacarpals dorsally and the proximal slideable pin 42 is located exactly over the pisiform and head of the scaphoid volarly. The remainder of the procedure is the same.

Additionally, measurements of creep of the ligament structures can be measured. The forearm and carpal metacarpal complex are stabilized by the apparatus as described above. Over time, the resistive force of the ligaments will gradually lessen as the ligaments relax under low force application. This relaxation response of the ligaments is known as creep. Studies can be made using the apparatus to determine optimal force values to be used in order to obtain maximum ligament creep.

Thus, this invention describes an apparatus and method for measuring the force and glide displacement exhibited by a person having a tendency towards carpal tunnel syndrome or else has symptoms of the same. It isolates measurement of the carpal joint without volitional muscular interaction with the ligament structure of the carpus.

While only a preferred embodiment has been illustrated and described, obvious modifications are contemplated within the scope of this invention and the following claims. For example, the measurement process could be automated so as to display force displacement values in real time and to compare the values obtained from a specific subject against either prior measurements for the same subject or against an average profile obtained by averaging the measurements taken from the population of subjects. Accordingly, the scope of the invention should be determined not by the embodiments illustrated but by the appended claims and their legal equivalents.

What is claimed is:

1. An apparatus for assessment of the glide in a live human body joint wherein a joint is formed of a forearm portion connected to a carpal-metacarpal portion by various ligament, tendon, and muscular tissues, the forearm portion having an ulna bone and a radius bone, the carpal-metacarpal portion having an ulnar side, and the tissues permitting shear, or translational, movement of the carpal-metacarpal portion relative to the forearm portion, the apparatus comprising the following components:
   (a) a means for stabilizing and aligning the forearm portion to a fixed plane defined by said apparatus;
   (b) a means for stabilizing and aligning the carpal-metacarpal portion to a movable plane parallel to said fixed plane and defined by said apparatus;
   (c) a means for providing bidirectional movement of said movable plane in a direction perpendicular, or normal, to said fixed plane, whereby either dorsal or volar glide between the forearm portion and the carpal-metacarpal portion is isolated; and
   (d) a means for measuring normal displacement between said fixed plane and said movable plane and for measuring resistance to movement exerted by the carpal-metacarpal portion as the carpal-metacarpal portion in said movable plane is moved in said normal direction with relation to the forearm portion in said fixed plane, said measurements being accomplished in the absence of a volitional component of force exerted by the muscular tissues.

2. The apparatus recited in claim 1, wherein the means for stabilizing and aligning the forearm portion to the fixed plane consists of
   (a) a base plate;
   (b) a first forearm pin row having a plurality of vertically oriented forearm pins in linear alignment fixedly connected to said base plate, whereby said fixed plane is established by said first forearm pin row in an orientation vertical and perpendicular to said base plate;
   (c) a second forearm pin row having a plurality of vertically oriented forearm pins in linear alignment, said second forearm pin row being parallel to said first forearm pin row and spaced a distance from said first forearm pin row to allow capture between said first forearm pin row and said second forearm pin row of the forearm portion oriented with the ulna bone resting against said base plate and the radius bone oriented outwardly from said base plate.

3. The apparatus recited in claim 2, wherein the plurality of vertically oriented forearm pins in the second forearm pin row are adjustable, whereby forearm portions of varying sizes may be accommodated between the first forearm pin row and the second forearm pin row.

4. The apparatus recited in claim 2, wherein the means for stabilizing and aligning the carpal-metacarpal portion to the movable plane consists of
   (a) a saddle constrained for bidirectional movement perpendicular to said first forearm pin row;
   (b) a first carpal-metacarpal pin row having a plurality of vertically oriented carpal-metacarpal pins in linear alignment fixedly connected to said saddle and parallel to said first forearm pin row, whereby said movable plane is established by said first carpal-metacarpal pin row in an orientation vertical and perpendicular to both said base plate and said saddle;
   (c) a second carpal-metacarpal pin row having a plurality of vertically oriented carpal-metacarpal pins in linear alignment, said second carpal-metacarpal pin row being parallel to said first carpal-metacarpal pin row and spaced a distance from said first carpal-metacarpal pin row to allow capture between said first carpal-metacarpal pin row and said second carpal-metacarpal pin row of the carpal-metacarpal portion with the ulnar side of the carpal-metacarpal portion resting against said saddle; and
   (d) a means for moving said saddle bidirectionally and perpendicular to said first forearm pin row, whereby shear, or translational, movement of the carpal-metacarpal portion with relation to the forearm portion is effected by the bidirectional movement of said saddle.

5. The apparatus recited in claim 4, wherein the plurality of vertically oriented carpal-metacarpal pins in the second carpal-metacarpal pin row are adjustable, whereby carpal-metacarpal portions of varying sizes may be accommodated between the first carpal-metacarpal pin row and the second carpal-metacarpal pin row.

6. The apparatus recited in claim 1, wherein the means for measuring force and displacement is accomplished over time.

7. A method of assessment of the state of a body joint of a live human being wherein a forearm portion is connected to a carpal-metacarpal portion by various ligament, tendon, and muscular tissues, the carpal-metacarpal portion being movable in a shear, or translational, maneuver perpendicular to the forearm portion without muscular contraction, the method comprising the steps of:

(a) fixing the forearm portion by a stationary support defining a fixed plane;

(b) restraining the carpal-metacarpal portion by a movable support defining a movable plane which is parallel to said fixed plane;

(c) dorsally moving the carpal-metacarpal portion by means of said movable support relative to the forearm portion restrained by said stationary support, whereby a shear maneuver between the distal radial ulna and the proximal carpal row is effected and resulting dorsal glide characteristics are isolated; and (d) measuring a displacement of said movable support and a resistance to movement of the carpal-metacarpal portion relative to the forearm portion, the displacement and the resistance being measured in the absence of an additional volitional component of muscular force.

8. The method of claim 7, wherein the step of fixing the forearm portion by the stationary support defining the fixed plane is accomplished by stabilizing and aligning the forearm portion to the fixed plane oriented vertically and defined by a plurality of dorsal vertical pins positioned on the dorsal side of the forearm portion and a plurality of volar vertical pins positioned on the volar side of the forearm portion, the pins being placed as follows:

(a) a first pin positioned dorsally just proximal to the radial distal head and the ulnar styloid;

(b) a second pin positioned volarly just proximal to the radial distal head and the ulnar styloid and opposite the first pin;

(c) a third pin positioned dorsally and approximately on the proximal one-third of the forearm; and (d) a fourth pin positioned volarly and approximately eight inches from the second pin.

9. The method of claim 7, wherein the step of restraining the carpal-metacarpal portion by a movable support is accomplished by stabilizing and aligning the carpal-metacarpal portion to a plurality of vertical carpal pins positioned on the dorsal side of the carpal-metacarpal portion and a plurality of vertical carpal pins placed on the volar side of the carpal-metacarpal portion, the pins defining the movable plane and being placed as follows:

1. a fifth pin positioned proximal to the epicondyles of the metacarpals dorsally;

2. a sixth pin positioned exactly over the pisiform and head of the scaphoid volarly;

3. a seventh pin positioned proximally to the distal end of the metacarpals dorsally; and 4. an eighth pin positioned proximally to the distal end of the metacarpals volarly.

10. The method recited in claim 7, comprising the additional steps of:

(a) comparing the values of displacement and resistance to historical values of these same measurements; and (b) assessing the severity of carpal tunnel syndrome onset from the comparison of values.

11. The method recited in claim 7, wherein a measurement of displacement and resistance is accomplished by taking the measurements over a plurality of discrete time intervals.

12. The method recited in claim 7, wherein successive measurements of force and displacement are taken after periods of time suitable for change to be exhibited in the resistance of the carpal ligaments and correlated to determine trends in the changing resistance of the carpal ligaments.

* * * * *